US005736630A

United States Patent [19]
Welner

[11] Patent Number: 5,736,630
[45] Date of Patent: Apr. 7, 1998

[54] SLIP FRICTION MEASUREMENT AND RECORDING APPARATUS

[76] Inventor: Jerome M. Welner, 1156 8th St., Manhattan Beach, Calif. 90266

[21] Appl. No.: 798,883

[22] Filed: Feb. 11, 1997

[51] Int. Cl.$^6$ .................................................... G01N 19/02
[52] U.S. Cl. ............................................................... 73/9
[58] Field of Search ............................................ 73/9, 10

[56] References Cited

U.S. PATENT DOCUMENTS

| | | |
|---|---|---|
| 3,977,231 | 8/1976 | Haehner et al. |
| 4,187,714 | 2/1980 | Cox et al. |
| 4,524,602 | 6/1985 | Moore. |
| 4,594,878 | 6/1986 | Abe et al. |
| 4,798,080 | 1/1989 | Brungraber. |
| 4,813,266 | 3/1989 | Nash. |
| 4,895,015 | 1/1990 | English. |
| 4,955,933 | 9/1990 | Sistonen. |
| 5,107,448 | 4/1992 | Nash. |
| 5,245,856 | 9/1993 | Pazzaglia et al. |

FOREIGN PATENT DOCUMENTS

| | | |
|---|---|---|
| 0052037 | 8/1986 | Japan. |
| 5573165 | 11/1977 | U.S.S.R. |

OTHER PUBLICATIONS

Dynamic Coefficient of Friction—7121 Method 1966.
Essential Design Criteria for an Ergonomically Sound Portable Slip—Resistance Tester 1985.
Ergonomic Analysis of Slip–Resistance Measurement Devices D. B. Chaffin 1985.
Std Test Method for Static Slip—Resistance of Footware ASTM F609-79 1989.
Measurement Products—Floor Sliperiness Tester.

*Primary Examiner*—Robert Raevis
*Attorney, Agent, or Firm*—Gordon A. Shifrin

[57] ABSTRACT

This invention is a compact and portable apparatus directed toward measuring the coefficients of both static and sliding friction or slip resistance occurring between two surfaces. Means are provided for determining and recording data to establish such friction accurately, repeatably, and in a form suitable for computer entry and data processing. Improvement over the prior art is provided with respect to mechanical configuration, ease of use, plus the acquisition and analysis of data, particularly for conditions involving wet or damp surfaces. A method is disclosed for essentially automatic determination of coefficient of friction.

17 Claims, 8 Drawing Sheets

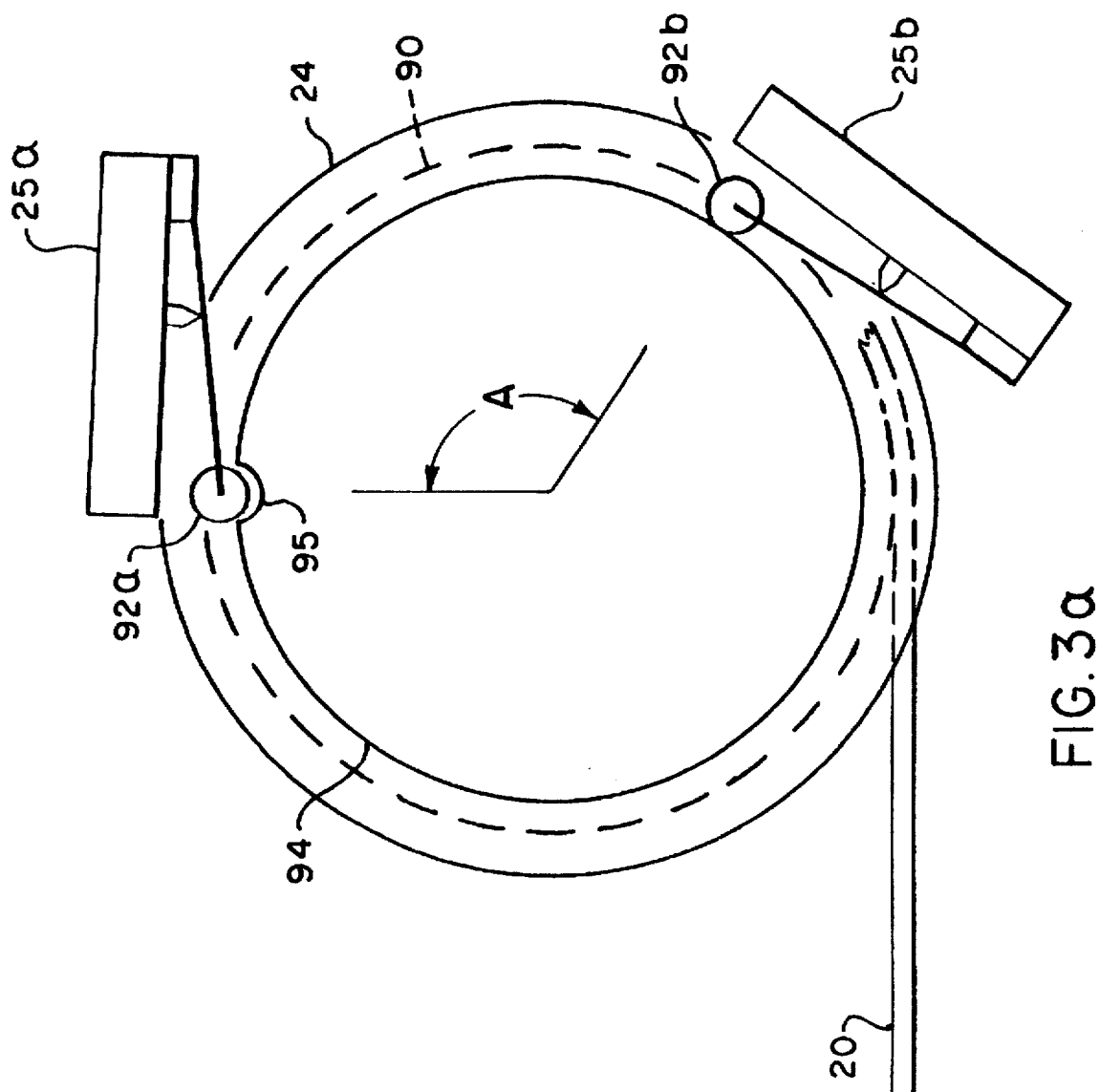
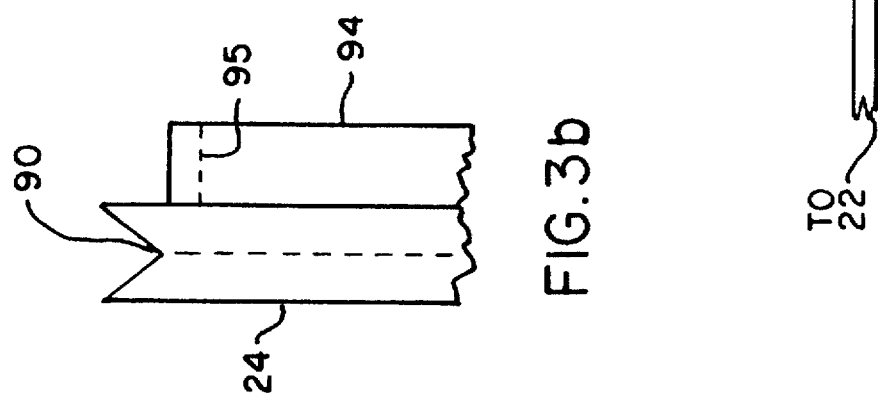

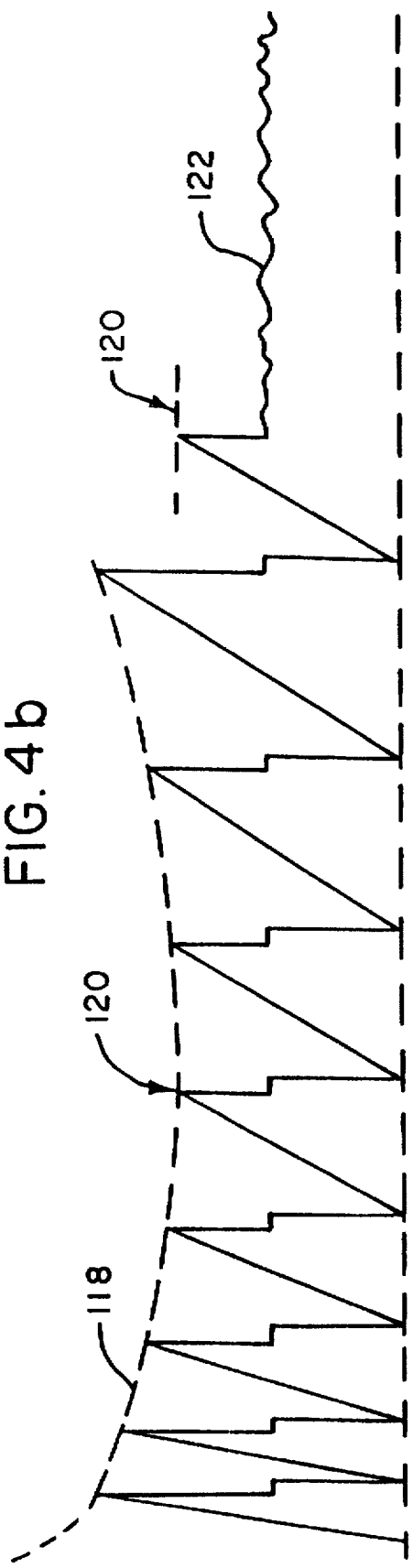
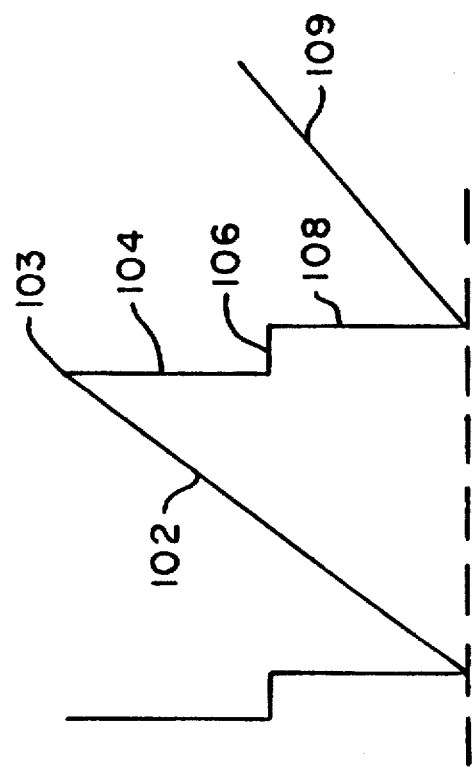
FIG. 4b
FIG. 4a

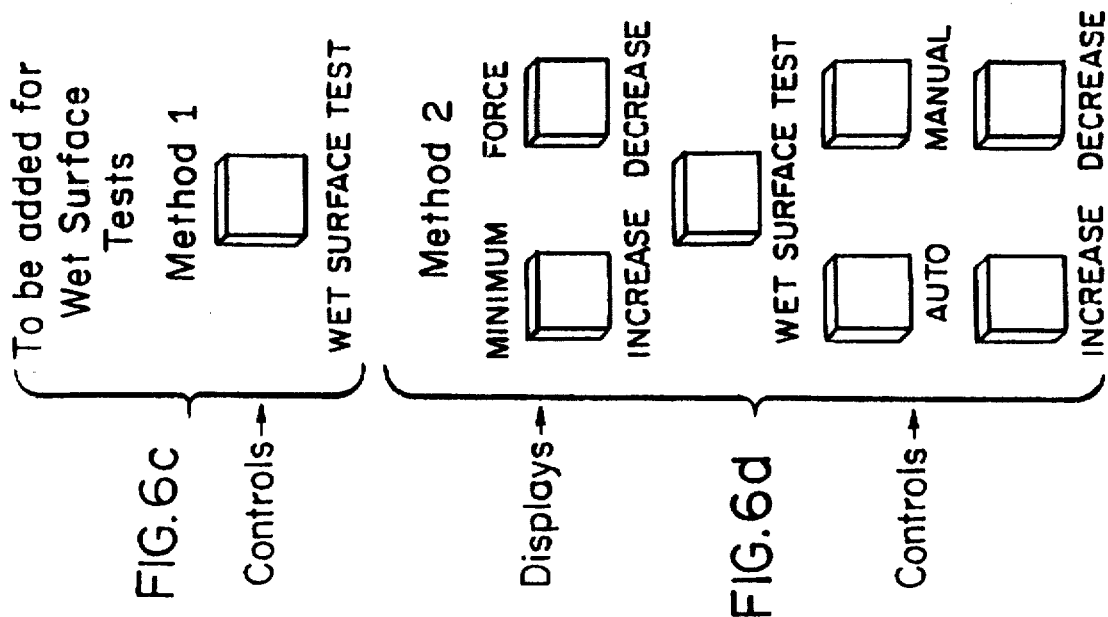
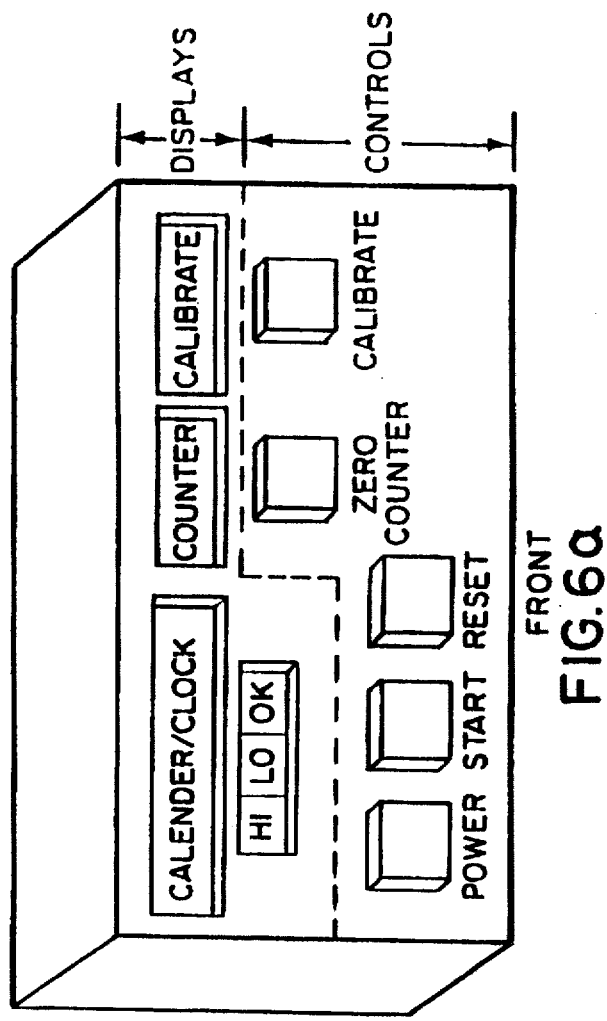
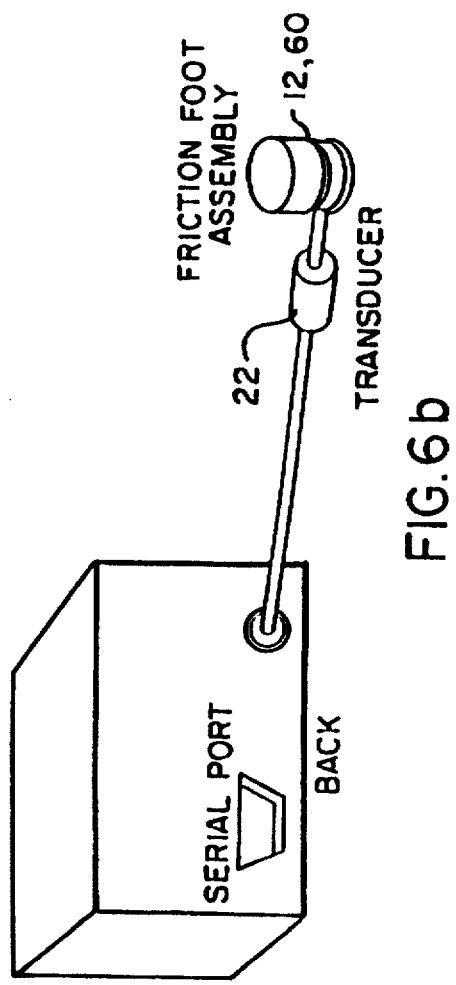

SLIP FRICTION MEASUREMENT AND RECORDING APPARATUS

This is a substitute application that is essentially a duplicate of the previous application with Ser. No. 08/486,001 (now abandoned) by the same inventor and originally filed Jun. 8, 1995.

FIELD OF THE INVENTION

The present invention relates to means for measuring the coefficient of sliding friction or slip resistance occurring between two surfaces and more particularly to means for determining and for recording such friction accurately, repeatably, and in a form suitable for both portability and for computer entry and processing. Special emphasis is directed toward such measurement with respect to surfaces that are wet or damp.

OBJECTIVES OF THE INVENTION

The main objective of this invention is to achieve an accurate and reproducible measurement and recording of the coefficient of sliding friction (or slip resistance) with respect to two specified surfaces in contact with each other as such friction occurs under various conditions, but where those conditions have been properly and carefully established. Special attention is given to such measurement when the surfaces involved are damp or wet. Another objective of this invention is to perform such measurement when the results are needed as evidence in legal disputes. A particular area of interest is to perform such measurements any place or on any surface where an individual may be injured while walking on such a surface. Thus, an objective of the invention is to provide a general purpose apparatus with special capability for measuring coefficient of both static and sliding friction and with particular features for such measurement under optimum conditions with respect to a test sample and a wet test surface. Also the invention could be used to establish specifications for safety features of related commercial products. A further objective is to generate such measurements that are precise and repeatable, that can be easily performed by non-technical personnel if necessary, and that once performed can be stored reliably within the instrument without loss until such time as they are needed for recording or analysis and can then be down loaded. A final objective is to provide a compact instrument that is light enough and portable enough for convenient use in the field.

BACKGROUND OF THE INVENTION

Friction occurs as a result of mechanical interaction along the interface between two surfaces in contact with each other. Friction is a ubiquitous physical phenomenon, occasionally undesirable, but without which many common actions and activities would be impossible. Most of the energy associated with friction is dissipated as heat, but some energy can act to remove particles from the two surfaces involved. The coefficient of static friction is generally defined as the ratio of (a) the lateral force (i.e. parallel to the surfaces) at which initial slip occurs to (b) the simultaneous normal force applied perpendicularly to the surfaces. The coefficient of sliding friction is defined in similar fashion with the same ratio, except that the ratio of forces is observed under the active conditions of relative movement between the surfaces after slip has occurred. The measurement of sliding friction is technologically significant in areas such as the safety of materials for shoes, walkways, automobile tires, and other areas where sliding friction is a vital and practical consideration.

Such measurements performed with respect to selected surfaces under specified conditions are of particular interest in certain areas of personal injury law suits or for testing commercial products with respect to safety under circumstances involving slip and fall where there is future potential for such suits. In such areas, it is often necessary to define and establish both the physical conditions and the associated measurements related to slip resistance in a manner that is objective and convincing. As an example in the legal area of interest, one circumstance would be where an individual wearing specified shoes walks on a specified wet surface such that slip has occurred and that such slip resulted in injury. It is essential that subsequent slip friction measurements be performed accurately and for conditions that establish, reproduce, and represent those conditions under which the disputed event occurred. Since this has been an important area of interest, many examples of prior art can be cited. The present invention provides substantial improvement over such prior art. In addition, the proposed embodiments are of significant technological value.

DESCRIPTION OF THE PRIOR ART

Earlier attempts intended to perform slip resistance measurements are inadequate in that they require or demand unreliable or excessive personal skill from the operator or for various reasons are inherently incapable of achieving satisfactory results.

Government Test Method 7121, "Dynamic Coefficient of Friction" dated Jun. 15, 1966 "(part of Federal Test Method Standard No. 501a) is intended for use in determining the dynamic coefficient of friction of resilient nontextile floor coverings with relatively smooth surfaces." In the apparatus described "a piece of rubber, leather, or other material is impacted onto and swept over the surface of the material being tested." The dynamic action is supplied with a pendulum having specified characteristics.

The University of Massachusetts, Department of Exercise Science, published a memorandum in May 1985 entitled "Essential Design Criteria for an Ergonomically Sound Portable Slip-Resistance Tester, and Other Field Measurement Considerations" in which legal and technical problems associated with slip resistance measurement are discussed in detail. Further extensive discussion of this problem is given in the periodical "Ergonomics" 1985, Vol 28, No 7 in an article entitled "Ergonomic Analysis of Slip-Resistance Measurement Devices."

The American Society for Testing and Materials has published Designation F 609–79, Static Slip Resistance of Footware Sole, Heel, or Related Materials by Horizontal Pull Slipmeter (HPS). Some difficulty of slip resistance measurement is recognized with the disclaimer that the proposed standard apparatus "does not purport to address all of the safety problems associated with its use." A useful definition of static slip resistance is provided: "the force required to cause one body in contact with another to begin to move." Three test specimens inserted in a steel block and taken from sheet material are employed. Careful preparation of materials and surfaces is required in the form of wiping and sanding. Other test conditions are carefully specified. The maximum value of resistance observed on a dial gage when movement occurs as a result of force being applied provides the final measurement of slip resistance.

Measurement Products of Altadena, Calif. manufactured a hand held drag type floor slipperiness tester. Test samples of the first material are attached to a weighted holder, which in turn is applied directly to the test surface of the second material. The holder is pulled horizontally across the test surface, and the required pulling force is measured and observed with a dial gage. Pulling speed and settling time are specified. Measurement Products also manufactured a portable pendulum impact type of slipperiness tester for measuring "dynamic coefficient of friction on relatively smooth walkway surfaces."

U.S. Pat. No. 3,893,330 issued to Shute et al describes " . . . an apparatus for measuring speeds and distances to determine the coefficients of friction between a tire of a braked vehicle wheel and a road surface." The scope of this invention is restricted to determining the coefficient of skidding friction for the conditions described. The apparatus includes a representative tire and additional equipment intended to measure speed and distance; the desired coefficient is determined through a formula relating those quantities.

U.S. Pat. No. 3,977,231 issued to Haehner et al measures only maximum static force, which is similar to the breakaway force described for the present invention. Sliding friction is not determined. No consideration is given to measuring wet or damp surfaces. The apparatus is not portable and cannot be used to observe a real test surface at an actual field site. There is no electronic storage of data.

U.S. Pat. No. 4,187,714 issued to Cox et al describes a friction sled pulled by hand over a test surface. The sled contains representative samples of an automobile tire and its associated tread, while the test surface is, for example, the actual road surface of interest. A spring scale measures the lateral force at which slip occurs as the sled is pulled, and the normal force is known through the total weight of the sled. The coefficient of sliding friction is computed from the ratio of these forces.

U.S. Pat. No. 4,524,602 issued to Moore describes an accident reconstruction device. Force is measured mechanically, there is no storage of data. Much skill is demanded of the operator.

U.S. Pat. No. 4,594,878 issued to Abe et al describes a device for measuring the coefficient of dynamic friction and for automatically recording the essential forces. The apparatus is applicable primarily to measurements associated with a road surface and a tire. Particular emphasis is placed on the relationship between dynamic coefficient of friction and the speed between the surfaces. The device is asserted to be applicable also to measurements involving shoes and a floor (page 7, line 36). In this device representative speed is achieved with a rotating disc brought up to speed with a motor. The measurement process consists essentially of observing the instantaneous torque required to drive the rotating disc when a second surface is applied with a known normal force. The electrical output is recorded as an X-Y plot of speed versus torque as the speed of the rotating disc diminishes to zero in response to friction.

U.S. Pat. No. 4,798,080 issued to Brungraber applies a normal force upon a nominally horizontal test surface through a tiltable articulated linkage whose critical tilt is a measure of the coefficient of friction. This device is designed for the measurement of the slip resistance of walkway surfaces that have been contaminated by the presence of water or other liquids. Normal and lateral forces are applied simultaneously on a prepared assembly of test surfaces. The ability to apply simultaneously both a normal force and a lateral force is featured, although they are derived as components of a single applied force. This ability is valuable as a means of simulating conditions of walking and provides a further advantage for testing wet surfaces in that fluid will not leak from between the test surfaces. Each of the two test surfaces represents a material of interest. A gradually increasing lateral force in the presence of a fixed normal force is achieved by tilting a mechanical linkage at variable angles until static friction can no longer prevent sliding and thus hold the test surfaces together. All forces are measured mechanically, and no storage of data is provided.

U.S. Pat. No. 4,813,266 issued to Nash employs a free standing sled of known weight whose under surface contains one material of interest and upon which is attached an accelerometer. The sled is placed upon the second surface of interest. A lateral impulse is applied to the sled with, for example, a hammer. In response to this impulse, the sled moves along the second surface and eventually comes to a stop. The signal from the accelerometer is observed electronically as a function of time. With suitable electronic recording and analysis of this data, the coefficient of friction can be determined.

U.S. Pat. No. 4,895,015 issued to English employs a drag sled, a stationery pulling mechanism, and a set of guide tracks for the sled. A servo assembly containing a direct current motor pulls the drag sled, Force is not recorded; the force necessary to pull the sled is measured purely mechanically and observed on a force gage having a visual display scale. Further, the foot assembly does not apply the normal force. Inaccuracies may accrue from gratuitous friction introduced as the weight moves in the channels.

U.S. Pat. No. 4,955,933 issued to Sistonen employs a wheel or tire that is pulled along the test surface. A spring applies resistive torque to the tire that just balances the frictional force on the tire at the moment that static friction is overcome and the tire begins to slide. The associated rotation of the resistive spring provides a measure of the sliding friction.

U.S. Pat. No. 5,107,448 issued to Nash is an improvement on the earlier patent issued to the same inventor. In the later patent, the required lateral force is applied with a stepping motor, and the test block is retained by linear springs whose displacement history ultimately provides a measure of both static and dynamic friction. A microprocessor is employed both to acquire data and to provide some control of the apparatus.

U.S. Pat. No. 5,245,856 issued to Pazzaglia et al employs a drag sled placed on the test surface. The drag sled is pulled by a cable attached to a combined pulling and measuring device that is held by the operator. Electronic components are used to acquire, process, and display the resulting data.

Soviet Union Patent (document number 05573165) by Gopo is a device specialized to measure simulated friction for skis upon snow. This device measures only sliding frictional force, without the ability to obtain coefficient of friction. There is no electronic storage of data. It is not a general purpose apparatus with special capability for such measurement with respect to wet surfaces.

Japanese Patent (document number 0052037) by Osaki is a specialized device to measure only coefficient static friction of a recording head upon a magnetic disk. There is no capability for measurements involving sliding friction. It is not a general purpose apparatus with special capability for measuring coefficient of sliding friction and with particular features for such measurement under optimum conditions with respect to a test sample and a wet test surface.

BRIEF DESCRIPTION OF THE INVENTION

The present invention is an apparatus for obtaining data to establish the coefficients of static and sliding friction between (1) a test surface and (2) a removable and interchangeable selected test sample. The invention provides improvement over the prior art with respect to ease of use and with respect to the acquisition and analysis of data, particularly, but not exclusively, for conditions involving wet or damp surfaces. The apparatus is simple to operate and requires minimal technical ability to obtain the required results. Combined electronic and mechanical means are provided to both measure and record critical data for subsequent computer analysis.

Measurement of sliding (or slip) friction for wet surfaces is sensitive to settling time, i.e. the interval beginning from the moment the wet test surfaces are placed together and extending to the instant when actual slip begins. It is important to prescribe settling time so as to control (a) the squeezing out of fluid from between the surfaces and (b) any microscopic and mutual mechanical molding or other undesired accommodation that might occur between the surfaces. Either of these effects might affect (more particularly increase) the observed friction and obscure the true values that are desired. Further, the lateral force that produces slip must not be applied and increased at a rate so rapid that inertial effects contaminate the results.

An important feature of this invention is that the normal force and the lateral force are produced from pure, independent, separate, and dedicated sources that are applied separately and individually.

With respect to wet surfaces, the special effort and methods as taught in this invention to establish conditions that are optimum for both test and measurement are absent in the prior art. The optimum condition for measurement generally refers to that condition which produces the minimum breakaway force for the particular test.

Special grooving can be introduced on the test sample expressly to capture and retain fluid while measuring friction between the test sample and a wet test surface.

The basic unit comprises a friction foot assembly (test package) connected mechanically to an electronically controlled pulling apparatus by means of a flexible cable or chain. The friction foot assembly containing a selected test sample that can be placed down upon the test surface so that the two surfaces of interest are in contact. The friction foot assembly then can be moved under electronic control across the test surface. The flexible cable is disposed essentially parallel to the test surface so that no vertical (i.e. normal) force component is introduced from this source. The friction foot assembly, the flexible cable, and the force transducer lie outside of the main cabinet that houses the remainder of the apparatus; the cabinet is provided with control and activation buttons available to the operator.

The flexible cable is pulled in tension by a pulley means whose total allowed rotation angle is controlled by limit switches. The pulley means is driven by a programmable electromechanical clutch means that in turn is driven by a constant speed motor. Torque to the pulley is supplied by the programmable clutch means; the clutch means is controlled by a variable voltage supplied by a power conditioner and an electronic master control unit. Thus, the tension applied to the cable is varied and is fully under electronic control.

Values of applied lateral force are measured continuously with the force transducer. The original force data in the form of the output values produced by the force transducer are amplified and sent to an analog to digital (A/D) converter, and sent from the A/D converter to the electronic master control unit, and then stored in a random access memory (RAM). Since normal force is also measured with the force transducer, this measurement is also stored in the RAM.

An electronic clock provides chronological input (date, time of day, etc.) to the electronic master control unit and to the RAM. Accumulated data stored in the RAM are made available to an output jack such as an RS 232 for subsequent computer processing or permanent recording and storage. A battery provides power to various electronic elements of the apparatus so that it can operate independently as a portable unit. A power switch controls the application of supply voltages from the battery to various elements of the apparatus.

Two methods are employed in the pursuit of data for slip friction. Method One has many features that are automatic in that for each sequence of tests, the friction foot assembly is placed upon the test surface only once, and subsequent tests and measurements are under the control of a microprocessor. An optimum rate of increase of lateral force associated with a minimum breakaway force are determined. Following this determination, a relatively prolonged period of lateral movement and data collection is employed to establish statistically significant data representative of slip friction. A relatively simple friction foot assembly can be employed with Method One.

With Method Two, the required instrumentation is simpler and less expensive, but the required operator involvement is greater than with Method One. Also as will be shown, the typical friction foot assembly itself is more complicated than that employed with Method One. With Method Two substantial operator action is required to determine the optimum application of lateral force. Subsequently, a prolonged period of lateral movement and data collection is employed to observe and establish slip friction.

BRIEF DESCRIPTION OF THE DRAWINGS

FIGS. 3a and 3b show details of the pulley means that applies tension to the flexible cable and includes rotation limit switches.

FIGS. 4a and 4b are diagrams showing the results of a typical measurement sequence to determine optimum test conditions as would be used on a wet surface and employing Method One.

FIGS. 6a, 6b, 6c and 6d illustrate typical control cabinets containing elements used for the slip friction measurement and recording apparatus as employed with both Method One and Method Two.

DETAILED DESCRIPTION OF THE INVENTION

This invention provides an approach to the measurement of coefficient of sliding friction or slip resistance that entails a number of attributes both mechanical and electronic not disclosed in the prior art. These attributes are described in this disclosure and in the accompanying drawings.

Figure 1:
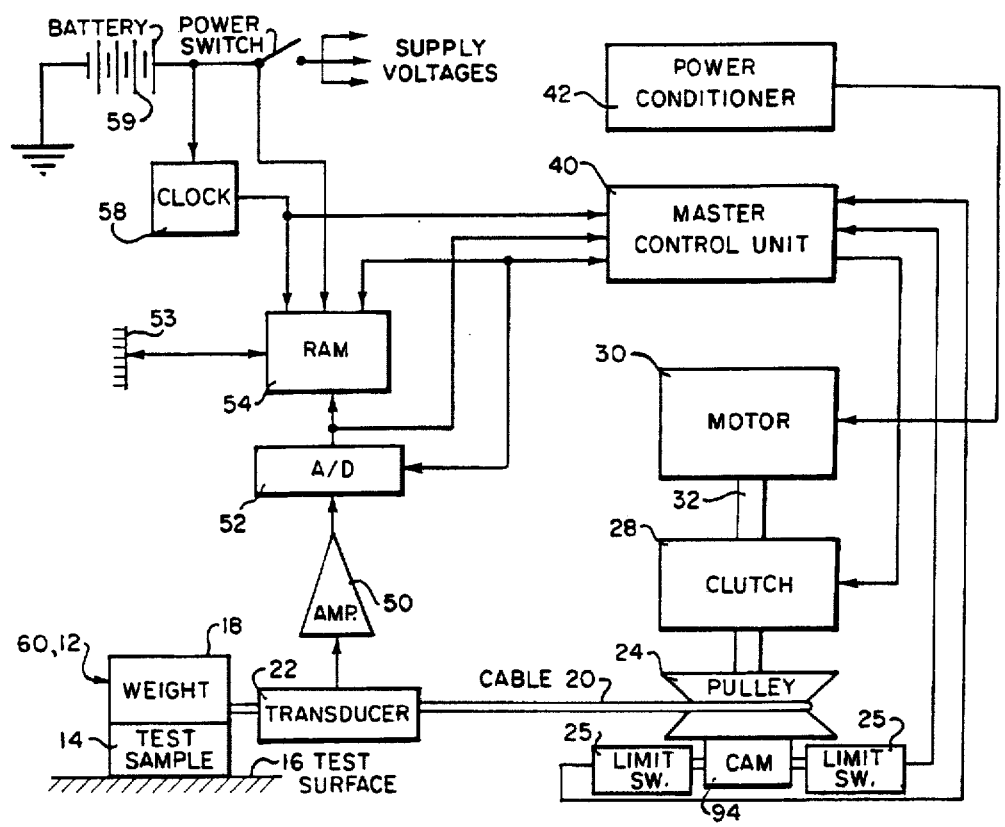
FIG. 1 is a block diagram that illustrates schematically the overall mechanical and electronic arrangement of a preferred embodiment of this invention.

FIG. 1 shows a block diagram of the overall arrangement of a preferred embodiment of the invention, showing some details in the form of an electronic block diagram. The representative friction foot assembly shown (subsequently described in two forms: 12 or 60) comprises a structural frame (not shown in this figure) holding weight 18 (that is both removable and interchangeable); also part of the friction foot assembly is selected test sample 14 (that is removable and interchangeable) that is placed against test surface 16 to perform a measurement. Test sample 14 is relatively thin and essentially flat.

To begin a friction measurement, the friction foot assembly is lowered upon test surface 16 in a controlled manner that will be described below. The friction foot assembly is pulled laterally along test surface 16 with tension supplied to flexible chain (or cable) 20 from pulley means 24.

The observed lateral force is generated in cable means 20 directly by the frictional resistance between the two surfaces under test. Pulley means 24 provides the lateral displacement required to maintain tension in cable 20. Torque delivered to pulley means 24 is supplied by constant speed motor 30 through programmable clutch means 28. Motor 30 and clutch means 28 are controlled by the master control means 40. In typical operation, as excitation of programmable clutch means 28 increases, the resulting torque in clutch means 28 delivered to pulley means 24 also increases, and lateral force to the friction foot assembly increases until breakaway occurs.

The instantaneous pulling force applied to friction foot assembly 12 or 60 is measured continuously with force transducer 22 that is interposed mechanically within the length of cable 20. Force transducer 22 can be any means that measures tension in cable 20, such as a strain gage or a piezo-electric sensor. If a force transducer requires electrical excitation, suitable wiring can be provided.

The first end of cable 20 is attached to friction foot assembly, while the second end of cable 20 is attached to pulley means 24 through circumferential wrapping. The combined configuration of the friction foot assembly and the pulley means is such that the cable is essentially parallel to the test surface. As a result, only lateral force and no normal force is introduced from this source. Pulley means 24 is provided with cam 94 (mounted circumferentially) and limit switches 25a and 25b, whose function is to control and limit the maximum rotation of pulley means 24 to a prescribed angle. Programmable clutch means 28 is driven by motor 30 through shaft 32.

Data supplied to and stored in the RAM 54 represent the amplified and processed original data in digital form from the force transducer and the pre-determined normal force. These data also represent and contain all critical parameters needed to determine the coefficients of both static and sliding friction for the various individual tests performed. Lateral force data from the A/D converter are sent to the electronic master control means. For each test performed, the computation of the ratio of lateral force to normal force that establishes coefficient of friction is accomplished by the electronic master control means and then stored in the RAM.

All raw data and computed results sent to the RAM 54 are stored there but are also available on demand to output connector (jack) 53 for subsequent recording or computer analysis. Thus there are no data limitations on the power or sophistication of any subsequent computer analysis. Sufficient memory is provided in the RAM 54, so that data and results obtained from several tests can be stored.

Electronic master control means 40 also provides electronic control throughout the instrument. Electrical power to motor 30 is supplied from battery 59 through power conditioner means 42. Power switch 57 applies power to those elements not requiring continuous electrical activation, but excluding such elements as the clock and the RAM. The electrical output of force transducer 22 is supplied to amplifier 50. That amplified signal is sent to A/D converter 52 that in turn sends its digital output to both the electronic master control means 40 and the RAM 54. Clock 58 provides chronological data (both date and time) to electronic master control means 40 and to RAM 54. Master control means 40 controls power conditioner means 42 and programmable clutch means 28. Control means 40 also provides electronic control to the RAM 54 and to A/D converter 52.

The total weight of the friction foot assembly is the actual normal force applied to the test sample. Similarly to the applied lateral force, this applied normal force is an essentially pure force completely separate and isolated. In preparation for all tests, this important value is determined in advance simply by suspending the friction foot assembly with cable 20, and noting the output of force transducer 22. The value of this normal force is then retained in the RAM 54. Since this dead weight is measured directly with the force transducer, the apparatus is self-calibrating with respect to applied normal force.

It is particularly significant that in this apparatus (a) both normal force and lateral force are measured with the same transducer, and (b) the desired coefficient of friction is calculated subsequently as a ratio of these two forces. As a result, overall accuracy of measurement is improved and systematic errors are reduced.

The lower surface of test sample 14 can be articulated with two sets of nominally parallel grooves, essentially normal to each other, and configured to an arbitrary degree of density. As the friction foot assembly is moved across the test surface, those areas of test surface 16 under the grooves are momentarily free of contact with the test sample. Thus, the use of grooving in the test sample will allow fluid on momentarily un-contacted portions of the test surface to return nominally to the original conditions of fluid coverage. As this occurs, the portion of test surface adjacent to a groove will be ready for contact with the corresponding un-grooved portion of the test sample as it is moved across the test surface and the test proceeds.

A further refinement of the grooves cut into the test surface is to configure the trailing faces of such grooves as ramps or small inclined faces essentially flat in form. Such ramps, employing an action similar to hydroplaning, will allow fluid that might have been squeezed out previously to be retained and re-established between the two surfaces under test.

Figure 7A:
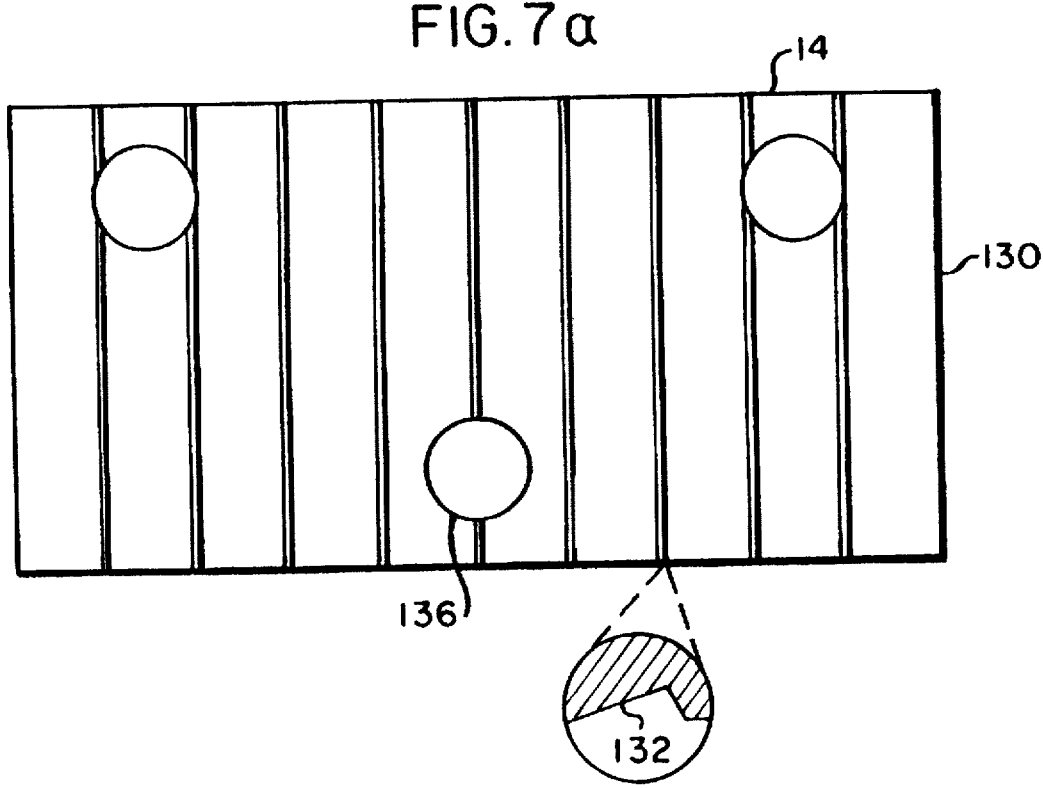
FIGS. 7a and 7b illustrate typical grooving that can be provided on the under side of the test sample.
Figure 7B:
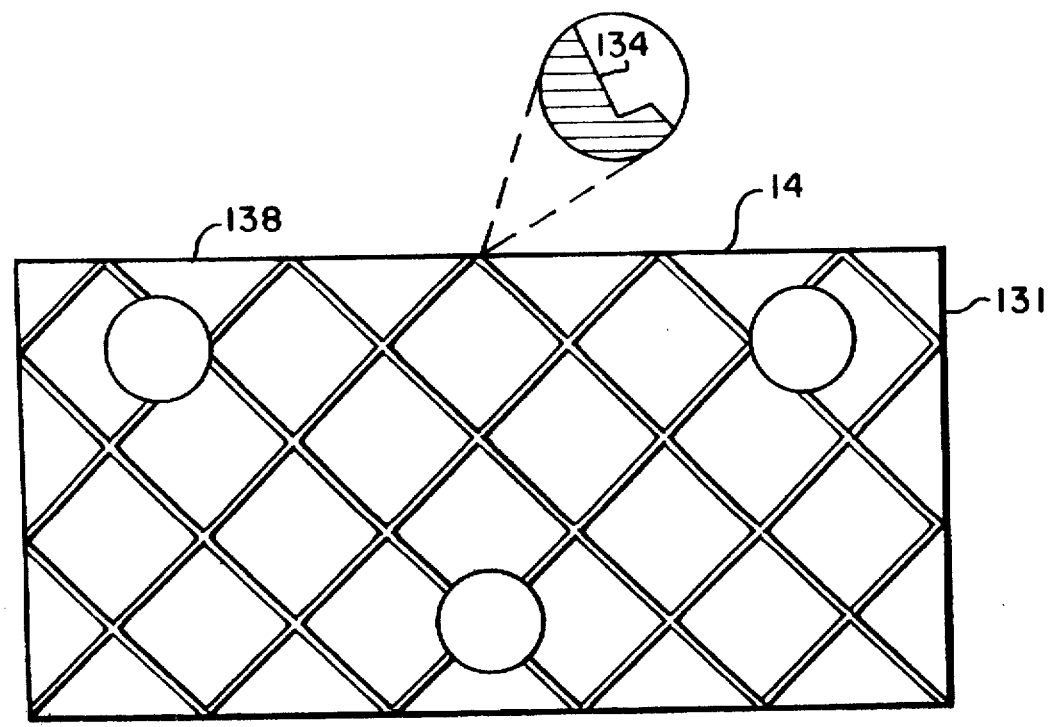

The layout pattern of these grooves may be of any form, but some examples are rectangular or diamond shaped with respect to the leading edge of the test sample. Typical patterns of groove articulation are illustrated in FIGS. 7a and 7b. FIG. 7a illustrates a typical rectangular groove pattern, where the two sets of grooves are essentially parallel and perpendicular to leading edge 130. FIG. 7b illustrates a typical similar diamond shaped groove pattern, where the two sets of grooves are arranged at an angle with respect to the leading edge of the test sample.

For a rectangular groove pattern, FIG. 7a illustrates a typical inclined face or ramp, which is shown as an enlargement from a groove. Inclined face 132 is oriented toward leading edge 130. For a diamond shaped groove pattern, FIG. 7b illustrates a similar enlargement of a typical inclined face 134 facing leading edge 131. In test sample 14, typical perforations 136 and 138 are provided to accommodate retractable feet 74.

Figure 2A:
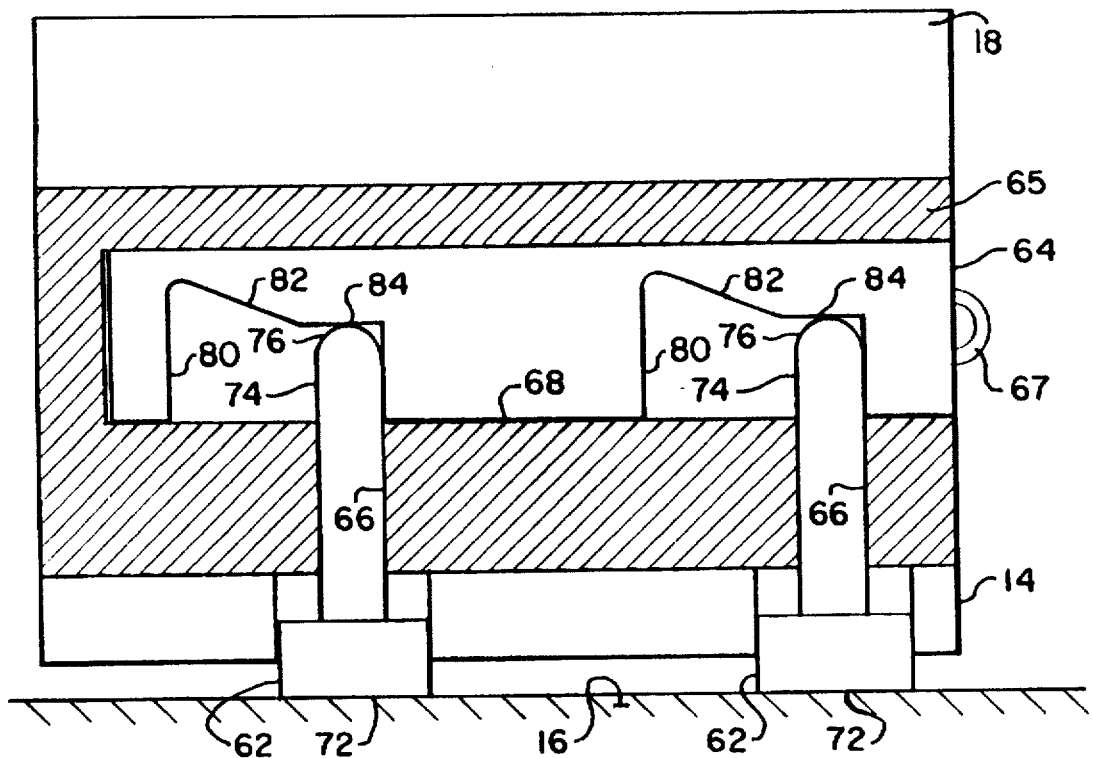
FIGS. 2a and 2b show details of the friction foot assembly as employed with Method Two.
Figure 2B:
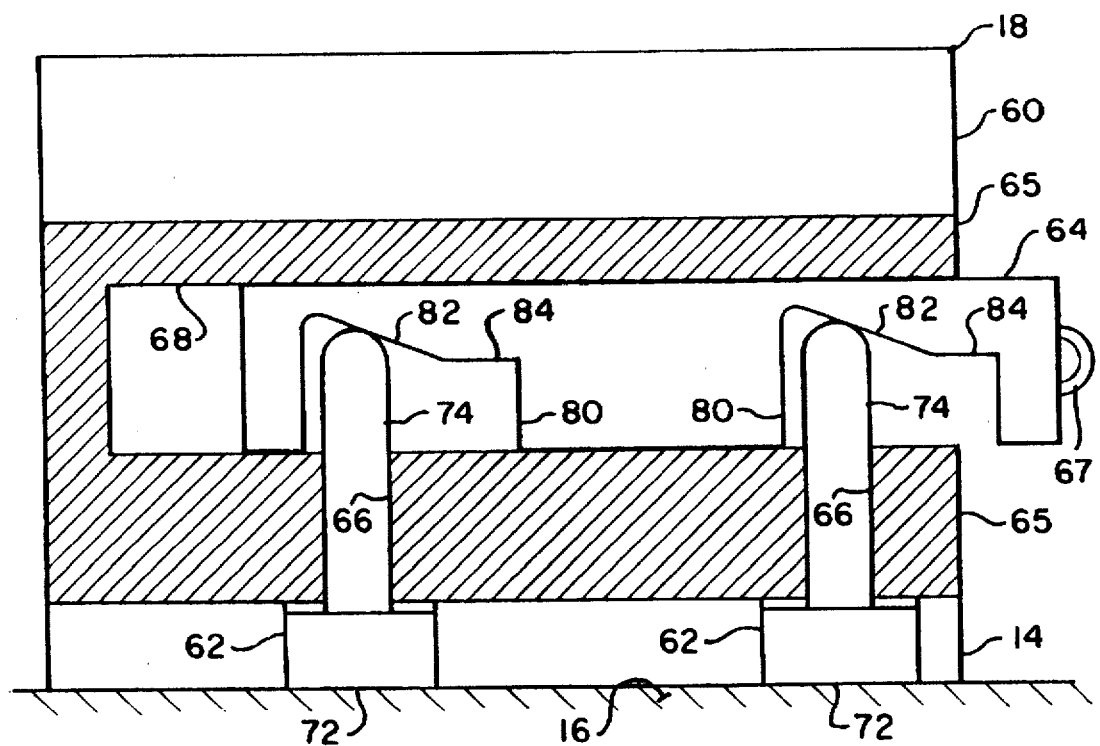

FIGS. 2a and 2b illustrate an example of a friction foot assembly 60 as it would be employed with Method Two. The friction foot assembly has the means for both applying and removing the test sample with respect to the test surface. In FIGS. 2a and 2b, weight 18 is removable and interchangeable so that a variety of weights can be employed. Weight 18 is situated in the upper portion of friction foot assembly 60. Selected test sample 14 also is removable and interchangeable. Test sample 14 is configured in the form of a relatively thin and essentially flat sample that lies at the bottom portion of friction foot assembly 60. Test sample 14 is suitably perforated to allow penetration of a plurality of retractable feet 62. The use of three retractable feet 62 is preferred because of its kinematic advantage of always defining a stable plane across test surface 16. The main function of the retractable feet is to elevate friction foot assembly 60 above test surface 16 to prevent contact with the test sample until the desired moment for beginning a test.

FIG. 2a shows friction foot assembly 60 with retractable feet 62 extended and thus elevating test sample 14 so as to be free of contact with test surface 16. FIG. 2b shows friction foot assembly 60 with retractable feet 62 fully retracted. In the condition shown, test sample 14 is resting upon test surface 16, and friction foot assembly 60 is ready for testing. With this configuration, particularly where wet surfaces are involved, initiation of contact and the beginning of the critical settling time interval can be controlled.

Interposed between weight 18 and test sample 14 is central block 64 situated within structural frame 65. Frame 65 is hollowed out to form internal containment chamber 68, which also acts as a mechanical guide for displacement (in sliding fashion) of central block 64. Essential details of a typical retractable foot 62 comprise support surface 72, shaft 74, and ball end 76.

In FIG. 2a, ball end 76 is introduced only schematically to indicate that a low friction end is required between the retractable feet and the central block. In place of the simple ball end 76, the use of rollers or any other advanced means for reducing friction between retractable feet 62 and central block 64 is entirely within the spirit and context of this invention.

The lower portion of structural frame 65 contains a plurality of perforations to form the plurality of guides 66 that (1) are matched to the number of retractable feet 62, and (2) are matched in form with shaft 74.

A typical form for the cross-section of guide 66 is cylindrical, and thus it provides a guide way to control displacement of a typical cylindrical shaft 74. If rollers or other advanced means are introduced to lower friction, some restriction on rotation of the retractable feet is necessary to preserve alignment in the cross-sectional form of (a) a combination of matching grooves and splines or (b) suitably matching non-circular shafts and guides.

Figure 8A:
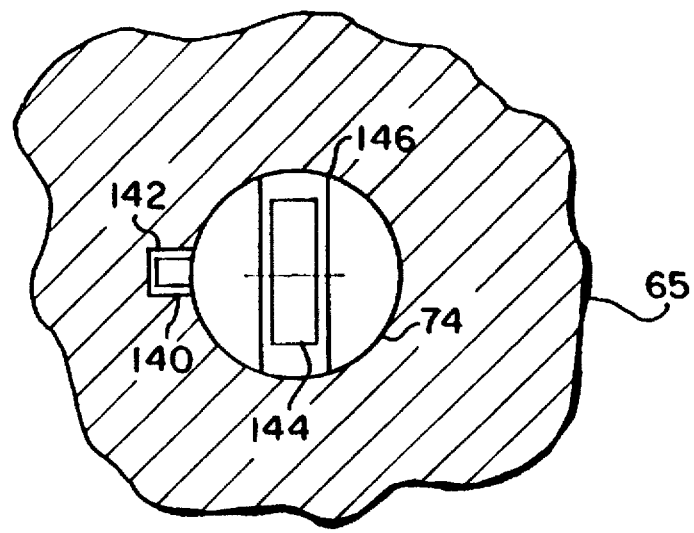
FIGS. 8a and 8b illustrate the use of rollers to produce a low friction end for the retractable feet; also shown are a spline and a matching groove to prevent rotation.
Figure 8B:
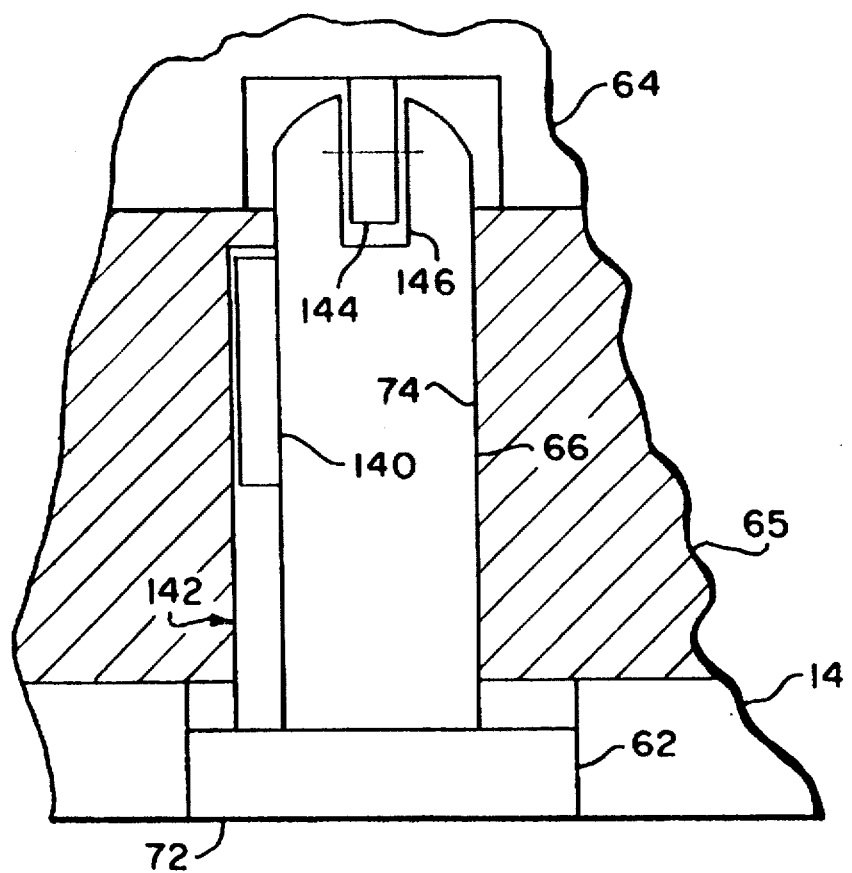

FIGS. 8a and 8b illustrate the use of a spline and a grooved guide to preserve rotational alignment and employing a roller to achieve a low friction end on the retractable feet. A typical example of a retractable foot is illustrated. FIG. 8a is a view along the axis of typical retractable foot 66. FIG. 8b is an elevation view of a retractable foot 66. To accommodate roller 144, the upper end of the shaft 74 is shown provided with slot 146. Roller 144 is resting against typical recess 80. Spline 140 fits into grooved guide 142, which prevents rotation of the roller with respect to recess 80 in central block 64.

The lower face of central block 64 is provided with a plurality of recesses 80 with openings that are disposed in a nominal vertical (i.e. downward) direction. The upper region of a typical recess 80 comprises a sloping portion 82 and a nominally horizontal portion 84.

As shown in FIG. 2b, central block 64 can be displaced to the right (i.e. for the extended or active position) by pulling with sufficient force on loop 67 with cable 20, such as would occur when a test is initiated. Central block 64 also can be displaced to the left (i.e. for the recessed or inactive position) to elevate the friction foot assembly and to prepare for the next test. Depending on the current position of central block 64, ball end 76 can contact either the sloping portion 82 or the nominally horizontal portion 84 of recess 80.

Central block 64 can be pulled to the right, as shown in FIG. 2b, to drop friction foot assembly 60 (and thus test sample 14) upon test surface 16. When central block 64 is positioned to the left as shown in FIG. 2a, the retractable feet 62 are extended so that ball end 76 contacts horizontal portion 84, and friction foot assembly 60 is elevated above test surface 16 so as to remove the test sample. When central block 64 is positioned to the right as shown in FIG. 2b, ball end 76 contacts sloping portion 82 of the recess, friction foot assembly 60 is not retracted. Test sample 14 then rests directly upon test surface 16, and retractable feet 62 are drawn within structural frame 65 so that support surfaces 72 are essentially flush with the lower surface of test sample 14 and thus are rendered essentially functionally inoperative.

FIGS. 3a and 3b shows details of pulley means 24 with its associated limit switches 25a and 25b. Pulley means 24 is provided with a typical V-notch 90 along its circumferential surface to accommodate cable 20 that is wrappably attached to the pulley, as shown in FIG. 3a. A detail of the circumferential V-notch and the location of cam 94 is shown in FIG. 3b. Cable 20 is connected to force transducer 22, which is not shown in this figure. Limit switch 25a is activated by roller 92a; similarly limit switch 25b is activated by roller 92b.

Attached concentrically to pulley means 24 is cam 94. In FIG. 3a roller 92a is in the extended position for switch 25a and is shown sitting in indentation 95; in this position switch 25a has sensed the presence of the said indentation. Switch 25b, on the other hand is shown with roller 92b in the compressed position for switch 25b, in which its electrical state is opposite to that shown for switch 25a.

Switches 25a and 25b are angularly displaced from each other by angle A, which is arbitrary and adjustable. Suitable means for angularly adjusting and clamping is provided for these switches. Thus angle A is established by the said angular displacement between switches 25a and 25b. This limited angular displacement of pulley means 24 prevents excessive windup of cable 20 during the course of testing for slip friction while pulling the friction foot assembly. The electrical status and activation of switches 25a and 25b is duly noted in electronic master control means 40. After the maximum allowed rotational displacement of angle A has been noted, pulley means 24 is rotated back to its initial position (basically that position shown in FIG. 3a) so that further testing can proceed.

As discussed above, two methods are disclosed for determining the coefficient of sliding friction or slip resistance. Mechanical differences provided in the friction foot assembly 12 or 60 can be employed to accommodate the requirements of each method, but the friction foot assembly 60 required for Method Two can also be employed for use with Method One.

Method One has many automatic features. Through the use of the previously established normal force and a preprogrammed sequence of operations and tests in Method One, the optimum rate of increasing lateral force is established. The optimum rate is that rate which achieves the minimum breakaway force. Optimum conditions are determined and selected with respect to both settling time and the rate at which force is applied to overcome inertia. Then, employing these optimum conditions, the friction foot assembly is pulled across the test surface for a relatively long period (e.g. more than two seconds) to generate a relatively large amount of data used to determine statistically significant parameters relating to slip friction.

FIGS. 4a and 4b illustrate the use of Method One on a typical run to determine the coefficients of both static and sliding friction or slip resistance with particular relevance for use upon a damp or wet surface. Note that when used with Method One, the friction foot assembly can be relatively simple in that it need not contain the displacement mechanism shown in FIGS. 2a and 2b, which is employed to elevate or drop the friction foot assembly upon the test surface. Optimum test conditions are determined with a programmed sequence of variable steps in which the rate of increase in lateral force is controlled and applied to the friction foot assembly. These varying rates are applied and are under the control of the apparatus illustrated in FIG. 1. In particular, friction foot assembly 12 or 60 is pulled by cable 20, whose tension (i.e. lateral force) is measured with force transducer 22 inserted within the length of cable 20. The rate of increase of applied lateral force (slope) is ultimately programmed and controlled through electronic master control means 40. Lateral force applied in this sequential manner increases and eventually reaches a level at which breakaway (initiation of slip) occurs.

FIG. 4a shows what happens for a typical application of lateral force. The lateral force is increased until breakaway occurs. Then at the moment breakaway occurs, there is a rapid decrease in the lateral force necessary to maintain motion. Thus once initiated, sliding friction can be maintained with a lateral force much lower than the breakaway force.

In FIG. 4a region 102 indicates the lateral force being increased at an essentially uniform rate. At the breakaway point 103, sliding friction begins, the required lateral force drops essentially immediately to the lower level required to maintain motion in a manner indicated by region 104. The force level 103 is a measure of static friction. The force level 106 corresponds to the level required to maintain sliding friction. Once sliding friction is detected and indicated, the next step in the test sequence can be initiated immediately by reducing the lateral force to zero and applying a new lateral force, but at a different rate of increase. Region 108 shows that the lateral force has been reduced to zero, so that a subsequent step in the test sequence can begin. Region 109 indicates the reduced slope (or rate) at which the lateral force is increased for a subsequent step in the sequence.

As shown in FIG. 4b, each individual step in the programmed sequence follows a pattern similar that shown in FIG. 4a. Instantaneous lateral movement is controlled at programmable electro-mechanical clutch means 28. As the sequence begins, lateral force (initially zero) is applied and increased at a relatively high rate where the corresponding sudden movement of the friction foot assembly introduces substantial inertial effects and a correspondingly higher breakaway force. As the automatic sequence proceeds, the rate of increase of lateral force is gradually decreased, and it is noted that the breakaway force also gradually decreases because of the lessening of the inertial effect. As the rate of increase of lateral force is further decreased with the sequence of successive programmed steps, however, it is noted that at some point the breakaway force begins to increase. This effect is the result of the settling time increasing into the region where significant amounts of fluid are being pressed out from between the test surface and the test sample; also the sample may be conforming mechanically to irregularities in the test surface.

The optimum rate of increase of lateral force occurs at the particular step where the breakaway force is observed to be at a minimum in an envelope curve 118 of the resulting breakaway forces. The minimum breakaway force is indicated as point 120 and is a measure of minimum static friction. This minimum effect occurs where the proper balance has been established between inertial effects (at higher rates of increase) and settling time (at lower rates of increase). The optimum rate of increase that produces the minimum breakaway force is noted and retained in memory and in RAM 54.

Thus, with the use of Method One, the system determines and applies the minimum force needed to overcome static friction and correspondingly applies the minimum acceleration to the friction foot assembly. In addition, the method allows determination of "stiction" forces. This follows because by providing a variable and controllable delay of lateral force build-up, the increase of coefficient of friction can be determined as the friction foot assembly sits upon a wet surface.

With the optimum rate established in this manner, a final measurement can be made. This final measurement is performed with an extended run that is initiated at the established optimum rate of increase for lateral force. After breakaway, which under these established conditions indicates optimum static friction, the lateral force required to maintain sliding (e.g. 106 in FIG. 4a) is applied continuously during the extended run. A typical duration of such an extended run would be on the order of two seconds or otherwise long enough to obtain adequate (i.e. statistically significant) and sufficient data to establish the desired sliding friction measurements for the specific test. The region observed for such an extended test run is indicated as 122.

Lateral force (that in this manner is required to overcome and maintain sliding friction) is continuously noted by the output of force transducer 22. In an actual test, this force may not be constant, but may fluctuate somewhat noisily within a narrow range. The results of such a test run, as indicated by the output of force transducer 22, is suitably recorded in RAM 54. This total series of operations can be repeated as often as required.

An entirely equivalent result would be obtained with Method One if the automatic sequence described were to be employed in reverse order, so that it was initiated with a relatively low slope (i.e. a relatively low rate of increase of lateral force) and then with the subsequent preprogrammed sequence of steps applied with gradually increasing slope.

Method Two is also appropriate for wet surfaces but arrives at an optimum settling time through a manually controlled sequence of observations of both applied lateral force and settling time. This optimum time is selected as an intermediate value between two prescribed time periods spanning a relatively narrow time interval: (a) a settling time known to be longer than a predetermined optimum settling time, and (b) one known to be shorter. Once the optimum settling time (and thus the optimum lateral force) is determined, then as with Method One, the friction foot assembly is pulled across the test surface for an extended period to obtain data necessary to determine applicable statistical characteristics for sliding friction.

Figure 5:
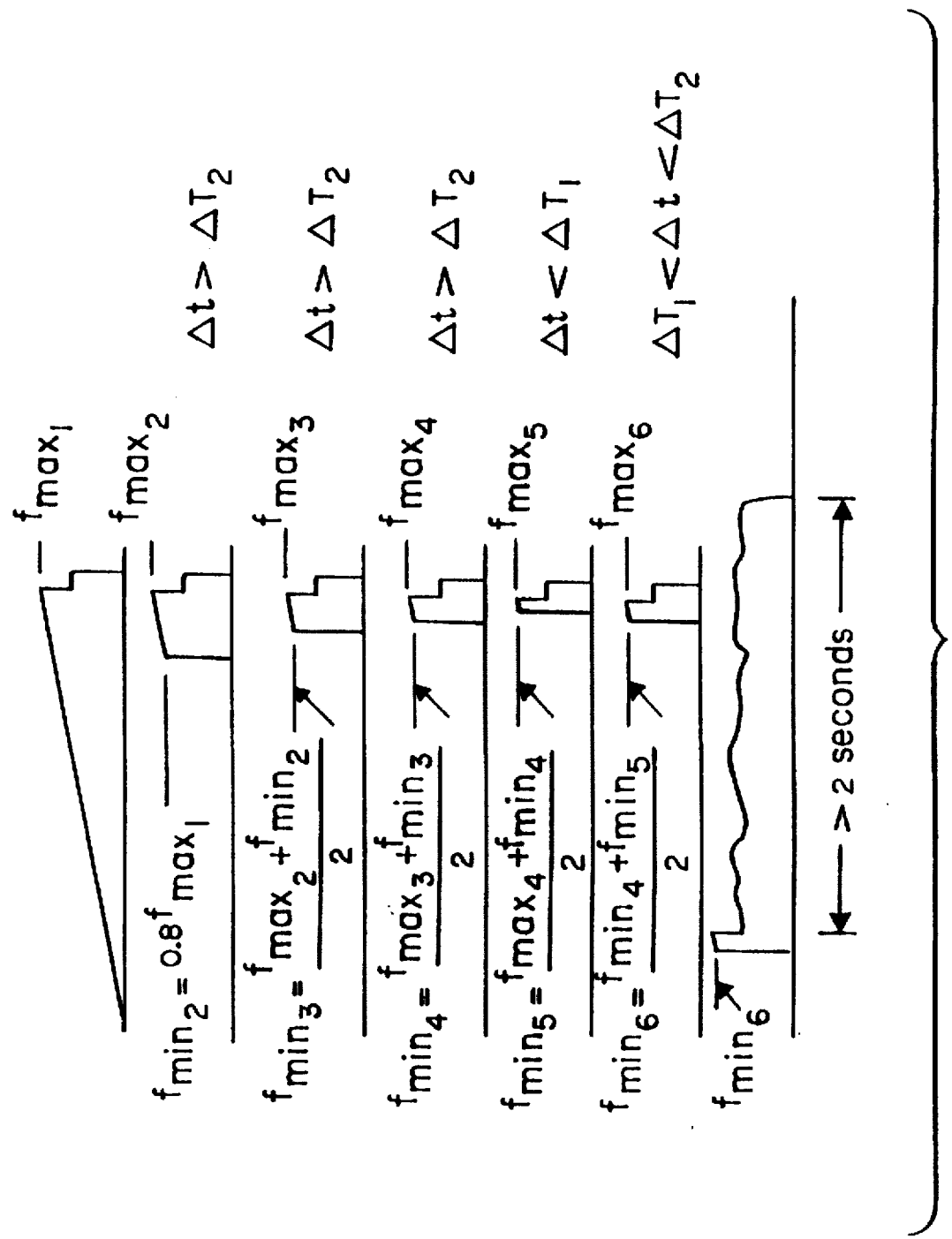
FIG. 5 is a diagram showing the results of a typical measurement sequence as would be used on a wet surface and employing Method Two.

FIG. 5 illustrates the use of Method Two on a typical run to determine the coefficient of sliding friction or slip resistance with particular relevance for use upon a wet surface. Method Two is essentially a manual procedure that approximately duplicates the automatic procedure and results of Method One. Note that the friction foot assembly employed for this method must be similar to and have the characteristics that are shown in FIGS. 2a and 2b. Thus, it must have the ability to be initially held away from the test surface and then set down upon the test surface at the instant the actual test begins. Before each test begins, central block 64 must be reset to its position as shown in FIG. 2a so that test sample 14 is retracted and elevated from test surface 16.

With Method Two, two time intervals are defined in terms of a previously established optimum settling time allowed for the friction foot assembly upon a wet surface. That is, the allowed optimum settling time must be greater than a predetermined lower interval delta-T1 and less than a predetermined upper interval delta-T2. A sequence of tests under manual control is employed with operations that proceed from observed results and that note both the settling time and the maximum pulling force before breakaway occurs. The pulling force is applied to the friction foot assembly 60 through cable 20 and measured with force transducer 22.

The intervals that bracket the optimum settling time (delta-T1 and delta-T2) will be determined by the manufacturer in advance for several typical surfaces and supplied with the apparatus. Any user, however, may determine these optimum times independently for any surface using the following techniques:

1. Starting at zero lateral force, increase lateral force until breakaway force is noted. Record both this force and the time taken to achieve the force. Repeat this process say ten times (to reduce random errors), and determine the average of breakaway forces and associated times.
2. Starting at 20 percent of the maximum average force (F-max) found in the above series of runs, increase lateral force until breakaway is noted (i.e. repeat step 1 except for the different starting force.).
3. Repeat step 1 for a series of test runs starting for example at 40 percent, 60 percent, 80 percent, 90 percent, 95 percent, and 99 percent of F-max as found in step 1.
4. Note and select which two of the above runs give the lowest breakaway forces. Then repeat step 1 starting at a force midway between the two selected runs that gave the lowest breakaway forces. For example if the lowest breakaway forces were noted at runs starting at 80 percent and 90 percent of the F-max as found in step 1, then at this point step 1 would be repeated at 85 percent of F-max.
5. Repeat step 4 (but continue to narrow the above force range) until the two starting forces are within one percent of each other or until measurement errors make it impossible to determine which breakaway force is lowest. This establishes a lowest (i.e. optimum) breakaway force for the surface under test.
6. Determine the average breakaway time of that run from step 5 that gave the lowest breakaway force. Delta-T1 is now specified as 0.8 of this time or this time minus 0.05 seconds, whichever is shorter. (If the computed value is less than zero, use zero.) Delta-T2 is specified as either (1) 1.2 of this time or (2) this time plus 0.05 seconds, whichever is greater.

The pulling force is first increased slowly until breakaway force is observed. This breakaway force is termed F-max-1.

Then, a pulling force substantially less than F-max-1 (set arbitrarily for example as 0.8 of F-max-1 and designated F-min-2) is applied initially and increased until breakaway occurs at F-max-2. Typically, F-max-2 will be less than F-max-1 because the settling time is less. F-min-2 is selected to be such that settling time will be greater than the predetermined interval delta-T2, which is known to be greater than the optimum settling time. Then an initial force (designated F-min-3) that is the average between F-max-2 and F-min-2 is applied and then increased until breakaway is observed at force F-max-3. The interval between the initial application of F-min-3 and breakaway (i.e. the settling time interval) at F-max-3 is noted. The next step is to apply an initial force (designated F-min-4) that is the average of F-max-3 and F-min-3 and is then increased until breakaway occurs at F-max-4. Again the settling time is observed and noted.

This sequence of tests is continued until an initial force is found such that the observed settling time before breakaway is less than delta-T1. If this settling time is also less than a predetermined minimum delta-T1, as is shown when the initial force F-min-5 is used, then the minimum force to be applied is decreased toward the last value that provided a settling time longer than delta-T1. This optimum minimum force is shown as F-min-6. In any particular test situation, the actual number of trials in the sequence required to determine this optimum force can differ from that shown in FIG. 5 and depends on the particular conditions of that test situation and cannot be determined in advance.

As a result of this typical sequence of operations with Method Two, an optimum settling time is bracketed between the predetermined intervals delta-T1 and delta-T2, and at the same time a corresponding narrow range for an optimum initial force has also been bracketed. The final test then establishes the coefficient of friction and slip resistance with an extended run (for example, two seconds or more) for which the optimum initial applied force, settling time, and breakaway force are chosen to lie within the established optimum range. During this final test, the continuous output of the force transducer is noted and recorded.

FIGS. 6a, 6b, 6c and 6d illustrate typical control cabinets containing elements required for use with the slip friction measurement apparatus as employed both with Method One and Method Two. These illustrations are merely representative of typical cabinets that would be employed, and suitable variations in design could be readily made by those skilled in the art without departing from the essential concept and spirit of this invention. The cabinet contains the following displays: Calendar/Clock, Counter, Calibrate, HI, LO, and OK. The cabinet also is provided with the following push buttons: Zero Counter, Calibrate, Power, Start, and Reset.

The basic cabinet shown in FIG. 6a could be used to test dry surfaces only; the system would supply only a linearly increasing tension to cable 20. Cabinets contain the electronic and control elements previously described. The friction foot assembly, cable, and force transducer are external to the cabinet as shown in FIG. 6b in a back view of the cabinet of FIG. 6a.

For measurements on wet surfaces, typical cabinets to be used with Method One or Method Two are similar except for the two additional and distinct sets of push buttons shown that are employed appropriately with each wet test method. These button arrangements are shown respectively in FIG. 6c and FIG. 6d.

A typical cabinet employed for Method One requires only a "Wet Surface Test" button (and its associated electronic control) in the control region of the front panel to initiate the preprogrammed sequence. This button is indicated in FIG. 6c. A typical cabinet employed for Method Two would use the set of buttons (and their associated electronic controls) indicated in FIG. 6d. Method Two requires in the display area of the front panel, one button to increase minimum force, and one to decrease minimum force. In the controls area typically five buttons are required: "Wet surface test," "Auto," "Manual," "Increase," and "Decrease."

Typical steps that the operator would employ in using the sliding friction measurement apparatus for various test conditions are described below:

1. Press the power switch. The counter display indicates how many runs have been stored since RAM was last read out and emptied. If the counter is at zero, the calibrator indicator lights up to tell the operator to calibrate the system. This requires weighing the friction foot assembly (FFA) so that tension forces may be employed in converting raw measurements into values for coefficient of sliding friction. If the operator chooses, the unit may be calibrated even if the counter is not set at zero.

Calibration steps are as follows:

2. Hang transducer and FFA from cable and press Calibrate button. The weight of the FFA is stored in the RAM so that the force measurements can be normalized.

3. Stretch cable and place FFA on surface to be measured. This step assures that displacements at the pulley along the cable are immediately and properly transferred to the FFA.

For dry surface test:

4. Press Start button. The counter is incremented. The system applies a slowly increasing tension to the cable until the FFA breaks free and slides for approximately two seconds. The following are digitized and stored in the RAM: time, date, run number, the weight of the FFA, and all cable tension data as measured by the force transducer.

If the peak force was within a predetermined optimum range in which the full resolution of the digitizer is used, the OK indicator lights up. If the force was beyond the ability of the system to measure it, the HI indicator lights up. If the peak force was low and did not use the highest bit of the digitizer, the LO indicator lights up.

5. Press Reset button. The cable is pushed back out of the box to prepare the system for the next run.

If the HI indicator lights up:

6a. Remove some weight from the FFA. Hang the FFA from the cable. Press the Calibrate button. The current weight of the FFA replaces the previous weight stored in the RAM, and the counter is decremented.

6b. Repeat steps 3, 4, and 5. System response is the same as it was for steps 3, 4, and 5.

If the LO indicator lights up:

6c. Add weight to the FFA. Hang the FFA from the cable. Press the Calibrate button. The current weight of the FFA replaces the previous weight stored in RAM, and the counter is decremented.

6d. Repeat steps 3, 4, and 5. System response is the same as it was for steps 3, 4, and 5.

7. Repeat steps 3 through 6 several times to obtain statistically valid data.

For wet surface test using Method One:

8. Press the Wet Surface Test button instead of the Start button. A high force impulse is applied to the FFA to break it free from the test surface. The force is reduced to zero immediately and then increased with a relatively high slope for the force time curve. Using feedback from the force transducer, time is determined that the shoe was stationary, the force/time history, and the maximum force required to move the FFA.

Force is reduced to zero and immediately increased with a slope that is slightly reduced from the previous run. Breakaway time, the force/time history, and the maximum force are determined.

The previous step is repeated with a reduced force/time slope until the maximum force increases considerably (e.g. greater than 20 percent more) or until the breakaway time exceeds one second.

The envelope curve of peak values is smoothed and a minimum peak value is noted. Using the slope that produced the minimum breakaway time, a complete force/time curve is run that typically continues for an interval greater than two seconds after the shoe starts slipping to obtain the coefficient of sliding friction.

The OK, HI, or LO indicator lights are used by the operator in the same manner as with the dry surface test.

For wet surface test using Method Two:

The clutch means is programmed so that the force will start at a minimum value and then increase continuously. The minimum value may be set by the operator or may be controlled by the internal processor. Between runs the operator must reset the foot assembly to extend the retractable feet so as to separate the test sample from the test surface.

9. Press the Wet Surface Test button.

10a. To have the system adjust the minimum force automatically, press the Auto button.

10b. To control the minimum force manually, press the Manual button.

Automatic Control:

The system starts with a relatively low minimum force. This force is increased until the FFA begins to slide. The maximum force is determined.

11. Reset the foot assembly. Press the Wet Surface Test button again. The minimum force is set to 80 percent of the maximum force found in the previous step. The force is increased until the FFA begins to slide. The maximum force and time from when the FFA was lowered until it started to slide are determined.

One of the following, a, b, or c, applies:

a. If the time is less than a predetermined minimum delta-T1, the minimum force is reduced to 50 percent of the separation from the previous value. The Decrease indicator lights up. Go to Step 11.

b. If the time is greater than a predetermined maximum delta-T2, the minimum force is increased to 50 percent of the separation from the maximum force found in the previous run. The Increase indicator lights up. Go to Step 11.

c. If the time lies between delta-T1 and delta-T2, both the Increase and the Decrease indicators light up. The OK, HI, and LO indicators will also light up. If the OK indicator is lighted, go to Step 12. Otherwise, increase or decrease the weight of the FFA, recalibrate, and repeat the run.

12. Reset the FFA. Press the Wet Surface Test button again. Using the previously determined minimum value, conduct a run that includes and acquires at least two seconds of data while the FFA is sliding. All data are stored in the RAM.

Manual Control:

The steps for manual control are the same as those for automatic control except that before each run, the operator must press the Increase or Decrease buttons as directed by which of the corresponding indicator lamps is lit. If the operator wishes to perform the two-second run without performing the indicated increase or decrease in minimum force, this may be done by pressing the Wet Surface Test button twice.

This invention may be embodied and practiced in other specific forms without departing from the spirit and essential characteristics thereof. Therefore, the present embodiments are considered in all respects as illustrative and not restrictive. The scope of the invention is indicated by the appended claims rather than the foregoing description. All substitutions, variations, and changes that come within the meaning and range of equivalency of the claims therefore are intended to be embraced therein.

What is claimed is:

1. An apparatus for measuring coefficients of static and sliding friction between (1) a test surface, and (2) a removable and interchangeable selected test sample and comprising in combination:

(a) a friction foot assembly whose total dead weight applies an essentially pure and separate normal force to said test surface; said friction foot assembly further comprising a removable and interchangeable weight, a structural frame that holds said weight plus said test sample, and further includes (1) an internal containment chamber that serves as a mechanical guide for a central block and (2) guides for a plurality of retractable feet; said friction foot assembly further comprising means for both applying and removing said test sample with respect to said test surface;

(b) means for applying and measuring an essentially pure and separate lateral force to said friction foot assembly comprising a cable means disposed essentially parallel to said test surface, the first end of said cable means is attached to said friction foot assembly and the second end of which is circumferentially attached to a pulley means by which said lateral force is applied to said cable means; inserted within the length of said cable is a force transducer that provides an electrical output proportional to tension in said cable, which is a measure of lateral force; wherein said force transducer can also be used measure the dead weight of said friction foot assembly to make the said apparatus self-calibrating with respect to applied normal force;

(c) a combined electronic and mechanical means for controlling, measuring, and recording said lateral force comprising a programmable electro-mechanical clutch means that can turn said pulley means and that is driven by an electric motor, that in turn is controlled by an electronic power conditioner means that in turn is controlled by an electronic master control means;

(d) said combined electronic and mechanical means further comprising an electronic amplifier that receives the output from said force transducer; the output of said amplifier is sent to an analog to digital converter, whose output is in turn delivered to a random access memory (RAM); wherein in the said RAM are stored and contained in digital form all amplified and processed original data from the said force transducer, normal force as pre-determined by the same force transducer, and results for coefficient of friction computed by the said electronic master control means; through an output connector, said processed original data and results are available on demand for subsequent recording and computer analysis;

(e) said combined electronic and mechanical means further comprising an electronic clock that provides chronological data (both time and date) that are sent to said random access memory and to said master control means, plus a battery to supply power;

(f) a cabinet means comprising said amplifier, said analog-to-digital converter, said random access memory, said master control means, said power conditioner means, said battery, said clock, plus control and activation buttons available to the operator.

2. The structural frame as disclosed in claim 1 is hollowed out to form said internal containment chamber and further contains a plurality of perforations to form said guides for said plurality of retractable feet wherein;

(a) said containment chamber is configured to enclose and guide said central block in sliding fashion;

(b) the lower face of said central block is configured with a plurality of internal recesses disposed in a nominal vertical direction; the upper region of each said recess contains a sloping portion and a nominally horizontal portion;

(c) each of said retractable feet is configured with a support surface, a shaft, and a low friction end;

(d) each said low friction end encounters the upper region of a corresponding said recess in said central block, in such a manner that each said retractable foot can be either (1) extended, to remove test sample from test surface when a low friction end encounters a said horizontal portion or (2) drawn within said central block to apply test sample to test surface when a low friction end encounters a said sloping region;

(e) said structural frame is configured and perforated with a plurality of guides corresponding in number to the plurality of retractable feet.

3. Retractable feet as disclosed in claim 1, wherein said low friction end is a low friction means such as a roller, and where in order to preserve rotational alignment, each said guide in said structural frame and the cross-section of each said shaft of each said retractable foot are configured in any form constituting a matching non-circular shaft and guide so as to restrict rotation of each of said retractable feet.

4. The said non-circular cross-section of said matching shaft and guide as disclosed in claim 3 consists of a spline on the shaft and a groove in the guide.

5. The test sample as disclosed in claim 1, wherein the form of said test sample is relatively thin and essentially flat, contains a plurality of perforations to allow passage of said retractable feet, and is located at the bottom portion of said friction foot assembly.

6. The lower surface of said test sample disclosed in claim 5 is articulated with two sets of essentially parallel grooves in an arbitrary pattern and with an arbitrary density; the trailing faces of said grooves are formed as inclined and essentially flat ramps so as to facilitate the retention of fluid between wet surfaces under test.

7. The articulated pattern of grooves as disclosed in claim 6 is rectangular, i.e. two, sets of grooves normal to each other and essentially parallel and perpendicular with respect to the leading edge of said test sample.

8. The said articulated pattern of grooves as disclosed in claim 6 is diamond shaped, i.e. two sets of grooves normal to each other but at an angle with respect to the leading edge of said test sample.

9. The force transducer as disclosed in claim 1 is a strain gage.

10. The force transducer as disclosed in claim 1 is a piezo-electric transducer.

11. The pulley means as disclosed in claim 1 further comprising angularly adjustable limit switches for controlling maximum allowed angular displacement.

12. The apparatus as defined in claim 1 is powered electrically by a battery to facilitate portability.

13. A method for establishing an optimum test condition to be employed for determining coefficients of static and sliding friction occurring between a test sample residing on a friction foot assembly and in contact with a wet test surface in which the normal force between said test sample and said test surface is previously established;

(a) then a lateral force is applied to said friction foot assembly employing a sequence of steps, and for each successive step of said sequence the rate of increase of said lateral force is varied;

(b) where for each said step of said sequence said lateral force is initially zero, then is gradually increased until breakaway occurs, then is reduced to zero, after which a subsequent step of said sequence is begun;

(c) where the successive steps of said sequence proceed so as to pass through and go beyond said optimum test condition; said optimum condition is determined and noted in the form of (1) the rate of increase of said lateral force that produces a minimum value of said breakaway force and (2) the value of said minimum breakaway force.

14. The method disclosed in claim 13 in which said sequence of steps is initiated with a step having a rate of increase of said lateral force greater than the said optimum rate, where the said sequence of steps proceeds with a gradually decreasing rate of increase of lateral force, and where said sequence passes through and beyond said optimum rate of increase as noted by a minimum value of breakaway force.

15. The method disclosed in claim 13 wherein said sequence of steps is initiated with a step having a rate of increase of said lateral force less than the said optimum rate, where the said sequence of steps proceeds with gradually increasing rate of increase of lateral force, and where said sequence passes through and beyond said optimum rate of increase as noted by a minimum value of breakaway force.

16. The method disclosed in claim 13 wherein upon determining said optimum condition for applying said lateral force, this said optimum rate of increase of lateral force is applied to said friction foot assembly, where after breakaway occurs and its value noted to indicate minimum static friction, the said lateral force is continued for a relatively long period so that statistically significant data on slip friction can be obtained for the particular samples under test.

17. The method disclosed in claim 13 wherein said lateral force is continuously measured and recorded.

\* \* \* \* \*